US006455557B1

(12) United States Patent
Pellegrini et al.

(10) Patent No.: US 6,455,557 B1
(45) Date of Patent: Sep. 24, 2002

(54) METHOD OF REDUCING SOMNOLENCE IN PATIENTS TREATED WITH TIZANIDINE

(75) Inventors: Cara A. Pellegrini, San Diego, CA (US); Paul Stark, Westmeath (IE)

(73) Assignee: Elan Pharmaceuticals, Inc., San Francisco, CA (US)

( * ) Notice: Subject to any disclaimer, the term of this patent is extended or adjusted under 35 U.S.C. 154(b) by 0 days.

(21) Appl. No.: 09/994,837

(22) Filed: Nov. 28, 2001

(51) Int. Cl.$^7$ .................. A61K 31/41; A61K 31/415
(52) U.S. Cl. .......................... 514/362; 514/385
(58) Field of Search ..................... 514/362, 361, 514/385

(56) References Cited

U.S. PATENT DOCUMENTS

| | | | |
|---|---|---|---|
| 3,843,668 A | 10/1974 | Neumann | |
| 4,053,617 A | 10/1977 | Eichenberger et al. | |
| 5,837,285 A | 11/1998 | Nakamichi et al. | 424/464 |
| 5,977,175 A | 11/1999 | Lin | 514/558 |
| 5,980,927 A | 11/1999 | Nelson et al. | |
| 6,110,494 A | 8/2000 | Clancy et al. | 424/461 |
| 6,143,325 A | 11/2000 | Dennis et al. | 424/468 |
| 6,214,370 B1 | 4/2001 | Nelson et al. | |
| 6,248,363 B1 | 6/2001 | Patel et al. | 424/497 |
| 6,268,389 B1 | 7/2001 | Esser et al. | 514/398 |
| 6,342,245 B1 | 1/2002 | Baert et al. | 424/451 |
| 2001/0007678 A1 | 7/2001 | Baert et al. | 424/464 |
| 2001/0024659 A1 | 9/2001 | Chen et al. | 424/457 |
| 2002/0006919 A1 | 1/2002 | Thosar et al. | 514/175 |

OTHER PUBLICATIONS

Hutchinson, D.E.; Modified Release of Tizanidine, A Review; vol. 17, No. 5, pp. 565–573 (1989).*
Holtebeck, B., "Tizanidine: An alternative in the Pharmacologic Treatment of Spasticity," *Journal of the Pharmacy Society of Wisconsin*, Mar./Apr. 2000: 26–31 (2000).
Young, R., "Tizanidine and spasticity," *Neurology* 45(12);2296–2296 (1995).
Roberts, R.C., et al., "Pharmacokinetics and pharmacodynamics of tizanidine," *Neurology* 44 (Supp 9): S29–S31 (1994).
Wallace, J.D., "Summary of combined clinical trials analysis of controlled clinical trials with tizanidine," *Neurology* 44(Supp 9): S60–S68 (1994).
Shellenberger, M.K., et al., "A controlled pharmacokinetic evaluation of tizanidine and baclofen at steady state," *Drug Metabolism and Distribution* 27(2): 201–204 (1999).
"Tizanidine," http://www.virtualdrugstore.com/ms/tizanidine.html.
"Pharmacology," http://www.southshoreneurologic.com/spas–manag/spas–pharmacology.html.
"Spasticity," http://www.wemove.org/spa mtop.html.
Wagstaff et al., Tizanidine, "A Review of its Pharmacology, Clinical Efficacy and Tolerability in the Management of Spasticity Associated with Cerebral and Spinal Disorders," ADIS Drug Evaluation, *Drugs*, 53(3), pp. 435–452 (Mar. 1997).
Zanaflex®, 2001 Physicians' Desk Reference (2001).
The Merck Index (1989).
Wesnes et al., "Effects of Sibutramine alone and with alcohol on cognitive function in healthy volunteers," *British Journal of Clinical Pharmacology*, 49, pp. 110–117 (2000).
Simpson et al., "The Cognitive Drug Research Computerized Assessment System for Demented Patients: A Validation Study, International Journal of Geriatric Psychiatry," *International Journal of Geriatric Psychiatry*, vol. 6, pp. 95–102 (1991).
Chapleo et al., "Heteroaromatic Analogues of the $\alpha_2$–Adrenoreceptor Partial Agonist Clonidine," *J. Med. Chem*, 32, pp. 1627–1630 (1989).
Smith et al., "Tizanidine in the management of spasticity and musculoskeletal complaints in the palliative care population, American Journal of Hospice & Palliative Care," *American Journal of Hospice& Palliative Care*, 17(1), pp. 50–58 (Jan.–Feb. 2000).

* cited by examiner

*Primary Examiner*—Theodore J. Criares
(74) *Attorney, Agent, or Firm*—Finnegan, Henderson, Farabow, Garrett & Dunner (57) ABSTRACT

An article and method for reducing somnolence in a patient receiving tizanidine therapy. Tizanidine may be administered in the form of an immediate release multiparticulate composition at or around the time food is consumed. The composition may be packaged in a container for distribution.

21 Claims, 1 Drawing Sheet

FIG._1

METHOD OF REDUCING SOMNOLENCE IN PATIENTS TREATED WITH TIZANIDINE

FIELD OF THE INVENTION is invention relates to a method and composition for reducing a side effect, namely somnolence, in patients receiving tizanidine drug therapy.

BACKGROUND OF THE INVENTION

Tizanidine is pharmacologically characterized as a central-acting alpha$_2$ ($\alpha_2$) adrenoceptor agonist which has myotonolytic activity useful in the treatment of spasticity in patients with cerebral or spinal injury, muscle spasm and pain. The imidazoline chemical structure of tizanidine is related to that of the anti-hypertensive drug clonidine and other alpha$_2$-adrenergic agonists, however therapeutic indications are different between the two. Tizanidine has one-tenth to one-fiftieth (1/50) of the potency of clonidine in lowering blood pressure while clonidine is ineffective in treating spastic conditions. This spectrum of activities is true of the 2-amino-imidazoline alpha$_2$ agonists in general where differences in the ring structures to which the amino group attaches cause marked differences in pharmacologic properties. For a general background on the alpha adrenergic receptors, see Robert R. Ruffolo, Jr., .alpha.-Adrenoreceptors: Molecular Biology, Biochemistry and Pharmacology, (Progress in Basic and Clinical Pharmacology series, Karger, 1991), wherein the basis of alpha$_1$/alpha$_2$ subclassification, the molecular biology, signal transduction (G-protein interaction and location of the significant site for interaction and ligand binding activity away from the 3'-terminus of alpha adrenergic receptors), agonist structure-activity relationships, receptor functions, and therapeutic applications for compounds exhibiting alpha-adrenergic receptor affinity is reviewed. See also Chapleo, C. B., R. C. M. Butler, D. C. England, P. L. Myers, A. G. Roach, C. F. C. Smith, M. R. Stillings & I. F. Tulloch, "Heteroaromatic Analogues of the .alpha$_2$-Adrenoreceptor Partial Agonist Clonidine", Journal of Medicinal Chemistry, Vol. 32 (1989), pp. 1627–1630.

Anti-spastic efficacy has been demonstrated for tizanidine in placebo-controlled trials, with reduction in mean muscle tone scores of 21 to 37% versus 4 to 9% for patients receiving placebo. Maximum effects in some studies have been demonstrated to occur within 2 hours of administration. In one clinical study, improvement in muscle tone occurred in 60 to 82% of tizanidine recipients, compared with 60 to 65% of baclofen and 60 to 83% of diazepam recipients, two other anti-spastic agents. Spasm frequency and clonus were also reduced by tizanidine. Wagstaff AJ; Bryson HM Drugs (NEW ZEALAND), Adis International Limited, Auckland, New Zealand, 53 (3) p435–52 (Mar 1997). The most common adverse effects associated with therapy are dry mouth and somnolence/ drowsiness. Muscle strength, as assessed by objective means, appears not to be adversely affected by tizanidine and subjective muscle weakness is reported less often by tizanidine recipients than by those receiving baclofen or diazepam.

Tizanidine can be classified generically as an amino-imidazoline adrenergic agent. In chemical nomenclature the molecule is described as 5-chloro-4-(2-imidazolin-2-ylamino)-2,1,3-benzothiadiazole and is also identified with Chemical Abstracts Registry number 51322-75-9 and in Merck Index (Eleventh Addition, Merck & Co., 1989) at monograph no. 9409. The compound may form pharmaceutically acceptable acid addition salts, and is used as the hydrochloride salt in Zanaflex®, the commercially available prescription product for treatment of spasticity in the United States. Synthesis of the compound and its myotonolytic properties are disclosed in U.S. Pat. Nos. 3,843,668 and 4,053,617 which are hereby incorporated by reference in their entireties.

Pharmacologic and electrophysiologic studies over the past 20 years have shown that tizanidine is a potent, centrally acting myotonolytic agent that principally affects spinal polysynaptic reflexes. This action arises from agonistic activity of the compound at noradrenergic alpha 2 receptors, resulting in both direct impairment of excitatory amino acid release from spinal interneurons and a concomitant inhibition of facilitatory coeruleospinal pathways. Similar alpha 2-receptor-mediated inhibition of interneuronal activity appears to underlie the additional antinociceptive and anticonvulsant activity of tizanidine reported in several species and test paradigms. Despite its structural and biochemical similarity to clonidine, the cardiovascular properties of tizanidine are mild and transitory in relation to its activity as a muscle relaxant. Smith H S; Barton A E, American Journal Of Hospice & Palliative Care (UNITED STATES), 17 (1) p50–8 (January–February 2000).

Pharmacokinetics

In studies conducted on a tablet formulation, tizanidine via oral administration was essentially completely absorbed and had a half-life of approximately 2.5 hours (coefficient of variation (CV)=33%). Following administration of tizanidine, peak plasma concentrations occurred at 1.5 hours (CV=40%) after dosing. Food increased $C_{max}$ by approximately one-third and shortened time to peak concentration by approximately 40 minutes, but the extent of tizanidine absorption was not affected. Tizanidine has linear pharmacokinetics over a dose of 1 to 20 mg. The absolute oral bioavailability of tizanidine is approximately 40% (CV= 24%), due to extensive first-pass metabolism in the liver; approximately 95% of an administered dose is metabolized. Tizanidine is widely distributed throughout the body; mean steady state volume of distribution is 2.4 L/kg (CV=21%) following intravenous administration in healthy adult volunteers. Tizanidine is approximately 30% bound to plasma proteins, independent of concentration over the therapeutic range. Zanaflex® monograph, 2001 Physicians' Desk Reference® Medical Economics Company, Inc. (publisher) Montvale, N.J.

Sedation/Somnolence

In multiple dose, controlled clinical studies, 48% of patients receiving any dose of tizanidine reported sedation as an adverse event. In 10% of these cases, the sedation was rated as severe compared to <1% in the placebo treated patients. Presently, patients are warned about performing activities requiring alertness, such as driving a vehicle or operating machinery while taking tizanidine. Patients are also instructed that sedation/somnolence may be additive when Zanaflex is taken in conjunction with other drugs (baclofen, benzodiazepines) or substances (e.g. alcohol) that act as CNS depressants.

The sedating effects may interfere with everyday activity. (vide infra, summary of Power of Attention studies), and the effect appears to be dose related. In a single dose study, 92% of the patients receiving 16 mg, when asked, reported that they were drowsy during the 6 hour study. This compares to 76% of the patients on 8 mg and 35% of the patients on placebo. Patients noticed the onset of this effect 30 minutes following dosing. The effect peaked 1.5 hours following dosing. Of the patients who received a single dose of 16 mg, 51% continued to report drowsiness 6 hours following dosing compared to 13% in the patients receiving placebo or 8 mg of tizanidine.

In the multiple dose studies, the prevalence of patients with sedation peaked following the first week of titration and then remained stable for the duration of the maintenance phase of the study. Zanaflex® monograph, 2001 Physicians' Desk Reference®, Medical Economics Company, Inc. (publisher) Montvale, N.J.

There remains an unmet clinical need for a pharmaceutical composition of tizanidine or its pharmaceutically acceptable salts and a method of administering a dosage form of tizanidine to a patient to reduce somnolence, a potentially dangerous side effect which often occurs with such therapy.

SUMMARY OF THE INVENTION

Figure 1:
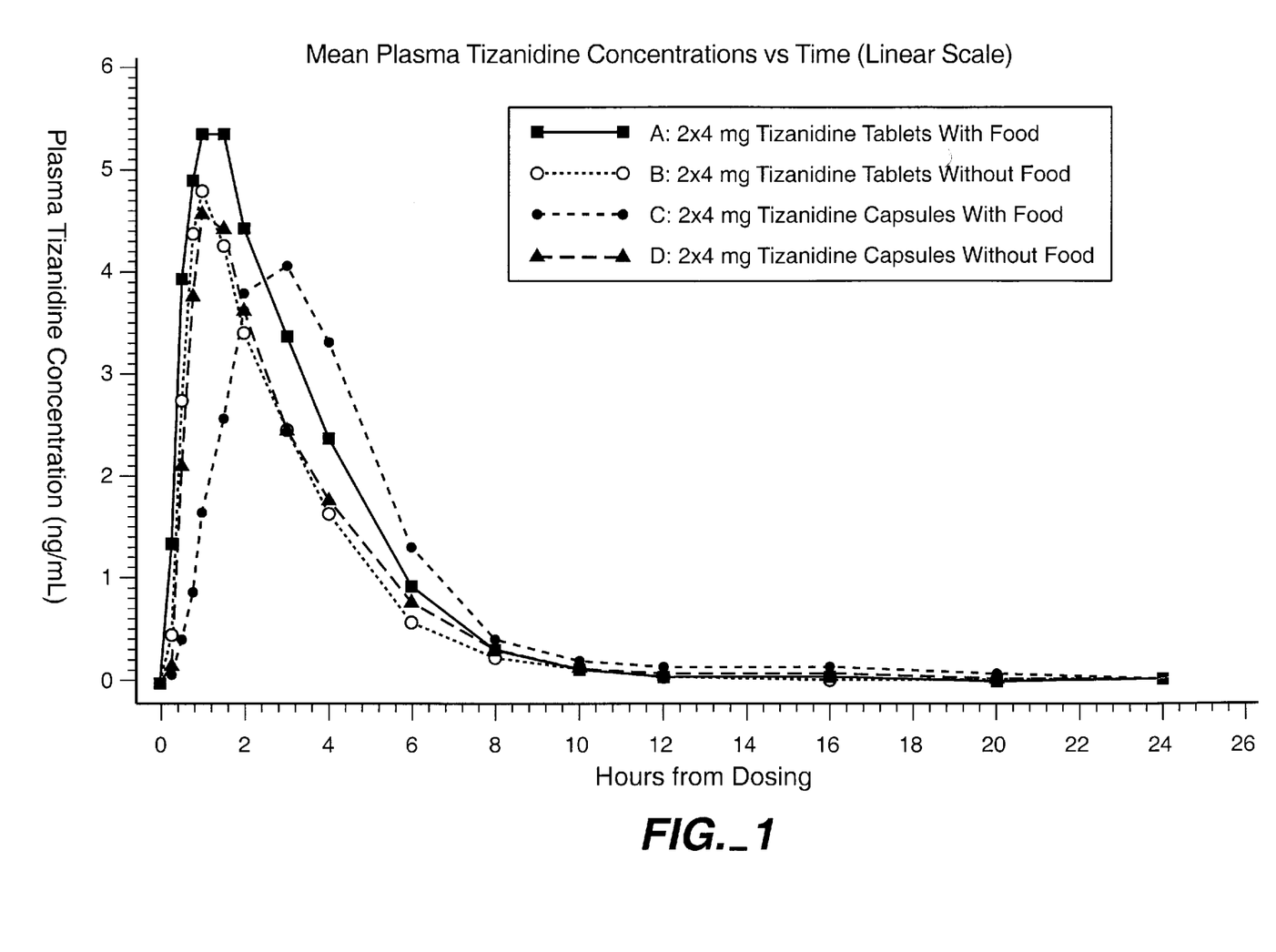
FIG. 1 is a plot of the plasma concentration of tizanidine in nanograms per milliliter versus the time elapsed from administration of the dosage form containing tizanidine. Four (4) plots are shown for tablet and capsule dosage forms administered with and without food.

Now it has surprisingly been found that administration of an immediate release multiparticulate pharmaceutical composition of tizanidine taken at or around the time food is consumed causes the least overall somnolence in patients receiving tizanidine therapy as compared with the tablet formulation administered with or without food. This result is wholly unexpected in comparison to earlier clinical studies of the tablet formulation which, when taken with food, significantly increases likelihood of somnolence.

One aspect of this invention is a method of reducing somnolence in a human receiving tizanidine therapy wherein the tizanidine is contained in an immediate release multiparticulate pharmaceutical composition, which method comprises administering a therapeutically effective amount of tizanidine to the patient with food.

Another aspect of the invention is providing a method of reducing the peak plasma level concentration attained in the blood stream of a patient receiving an immediate release multiparticulate pharmaceutical composition, which method comprises administering a therapeutically effective amount of tizanidine to the patient with food.

Preferably the therapeutic amount is between about 0.5 mg to about 12 mg, and more preferably between about 2 mg to about 8 mg, with the most preferred dosage being between about 2 mg and about 6 mg. Unit dosage forms are preferred.

Preferably the food is a solid food with sufficient bulk and fat content that it is not rapidly dissolved and absorbed in the stomach. More preferably the food is a meal, such as breakfast, lunch or dinner. Advantageously the dosage is administered to the patient between about 30 minutes prior to about 2 hours after eating a meal, most advantageously the dosage is administered at substantially the same time as the eating of the meal. The terms "without food", "fasted" and "an empty stomach" are defined to mean the condition of not having consumed solid food for about 1 hour prior to until about 2 hours after such consumption.

Yet another aspect of this invention is providing information to prescribing physicians and patients receiving tizanidine therapy useful in limiting somnolence as a side effect when taking tizanidine in immediate release multiparticulate or tablet dosage form.

Still another aspect of this invention is an article of manufacture that comprises a container containing an immediate release pharmaceutical composition comprising tizanidine or a pharmaceutically acceptable salt thereof, wherein the container holds preferably the tizanidine (or its salt) composition in unit dosage form and is associated with printed labeling instructions advising of the differing absorption and therefore varying somnolence side effects when a particular pharmaceutical composition is taken with and without food.

A further inventive aspect is providing an immediate release multiparticulate pharmaceutical composition including a therapeutic amount of tizanidine in multiparticulate form having similar bioavailability to the tablet form without an increased likelihood of somnolence when taken with food and/or less somnolence associated with its use if taken with food than a tablet formulation of same dosage strength.

An immediate release composition is one which allows all or substantially all of the tizanidine to be released from the dosage form in less than 60 minutes. Preferably, at least 75% of the tizanidine is released in less than 60 minutes. More preferably, at least 75% of the tizanidine is released in 30 minutes.

The term "multiparticulate" as used herein means a plurality of discrete particles, pellets, mini-tablets and mixtures or combinations thereof. If the oral form is a multiparticulate capsule, such hard or soft gelatin capsules can suitably be used to contain the multiparticulate. Alternatively a sachet can suitably be used to contain the multiparticulate.

Preferably, the immediate release multiparticulate pharmaceutical composition is in the form of a population of immediate release beads having tizanidine layered over non-pareil seeds. Such multiparticulates are preferably filled into an immediate release capsule to provide the correct dosage level. The composition of the present invention can be prepared by any known means. Preferably, the therapeutic amount of tizanidine is between about 0.5 mg to about 12 mg, and more preferably between about 2 mg to about 8 mg, with the most preferred dosage being between about 2 mg and about 6 mg.

The immediate release pharmaceutical composition of the present invention can have a potency (mg tizanidine/g multiparticulates) that provides an acceptable volume of multiparticulates to be filled in a preferred capsule size to a desired dosage level. The potency can vary based on the desired dosage and the size of the preferred capsule. The present composition can have a potency of between about 5 and about 100 mg tizanidine per gram of multiparticulates. Preferably, the composition has a potency of between about 10 and about 40 mg tizanidine per gram of multiparticulates. More preferably, the composition has a potency of between about 20 and about 30 mg tizanidine per gram of multiparticulates.

The composition of the present invention may include also conventional excipients of the type used in pharmaceutical compositions. For example, the composition may include pharmaceutically acceptable organic or inorganic carriers suitable for oral administration. Examples of such carriers include: sugar spheres, diluents, hydrophilic polymers, lubricants, glidants (or anti-adherents), plasticizers, binders, disintegrants, surfactants and pH modifiers.

Suitable diluents include microcrystalline cellulose, lactose, sucrose, fructose, glucose dextrose, or other sugars, dibasic calcium phosphate, calcium sulphate, cellulose, ethylcellulose, cellulose derivatives, kaolin, mannitol, lactitol, maltitol, xylitol, sorbitol, or other sugar alcohols, dry starch, dextrin, maltodextrin or other polysaccharides, inositol or mixtures thereof.

Suitable hydrophilic polymers include hydroxypropylmethyl cellulose, carbomers, polyethylene oxides, hydroxypropyl cellulose, hydroxyethyl cellulose, carboxymethylcellulose, sodium carboxymethylcellulose, carboxyvinylpolymers, polyvinyl alcohols, glucans, scleroglucans, mannans, xanthans, carboxymethylcellulose and its derivatives, methylcellulose and, in general, cellulose, crosslinked polyvinylpyrrolidone, carboxymethyl starch, potassium methacrylate-divinylbenzene copolymer, hydroxypropylcyclodextrin, alpha, beta, gamma cyclodextrin or derivatives and other dextran derivatives, natural gums, seaweed extract, plant exudate, agar, agarose, algin, sodium alginate, potassium alginate, carrageenan, kappa-carrageenan, lambda-carrageenan, fucoidan, furcellaran, laminarin, hypnea, eucheuma, gum arabic, gum ghatti, gum karaya, gum tragacanth, guar gum, locust bean gum, quince psyllium, flax seed, okra gum, arabinogalactin, pectin, scleroglucan, dextran, amylose, amylopectin, dextrin, acacia, karaya, guar, a swellable mixture of agar and carboxymethyl cellulose; a swellable composition comprising methyl cellulose mixed with a sparingly cross-linked agar; a blend of sodium alginate and locust bean gum; and the like.

Suitable glidants (or anti-adherents) include colloidal silica, fumed silicon dioxide, silica hydrogel, talc, fumed silica, gypsum, kaolin and glyceryl monostearate.

Suitable plasticizers include acetylated monoglycerides; butyl phthalyl butyl glycolate; dibutyl tartrate; diethyl phthalate; dimethyl phthalate; ethyl phthalyl ethyl glycolate; glycerin; propylene glycol; triacetin; citrate; tripropioin; diacetin; dibutyl phthalate; acetyl monoglyceride; polyethylene glycols; castor oil; triethyl citrate; polyhydric alcohols, glycerol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, glyceryl monocaprylate, glyceryl monocaprate.

Suitable binders include starches, hydroxypropylmethyl cellulose, hydroxypropyl cellulose, ethyl cellulose, polyvinyl pyrrolidone, acacia, guar gum, hydroxyethylcellulose, agar, calcium carrageenan, sodium alginate, gelatin, saccharides (including glucose, sucrose, dextrose and lactose), molasses, extract of Irish moss, panwar gum, ghatti gum, mucilage of isapol husk, carboxymethylcellulose, methylcellulose, veegum, larch arbolactan, polyethylene glycols, waxes and mixtures thereof.

Suitable disintegrants include starches, sodium starch glycollate, crospovidone, croscarmellose, microcrystalline cellulose, low substituted hydroxypropyl cellulose, pectins, potassium methacrylate--divinylbenzene copolymer, polyvinylalcohol, thylamide, sodium bicarbonate, sodium carbonate, starch derivatives, dextrin, beta cyclodextrin, dextrin derivatives, magnesium oxide, clays, bentonite and mixtures thereof.

Suitable surfactants include nonionic surfactants such as sorbitan sesquioleate, polyoxyethylene sorbitan monooleate, polyoxyethylene monostearate, glycerol monostearate, propylene glycol monolaurate, polyoxyethylene lauryl ether, polyoxyethylene cetyl ether or polyoxyethylene hydrogenated castor oil; and ionic surfactants such as sodium dodecyl sulfate or benzalkonium chloride; and the like.

Suitable pH modifiers include organic acids such as citric acid, fumaric acid, tartaric acid, succinic acid, ascorbic acid, acetic acid, malic acid, glutaric acid and adipic acid; salts of these acids; salts of inorganic acids and magnesium hydroxide.

Other aspects will become apparent upon a careful reading of this patent specification and claims.

Assessment of Somnolence by Cognitive Impairment Measurements and Pharmacokinetic (PK) Studies Somnolence following doses of tizanidine was studied by assessing the impact of somnolence on cognitive function as measured by Power of Attention (as defined herein) after each study treatment. To demonstrate bioavailability of 2×4 mg tizanidine capsules relative to the commercial 2×4 mg Zanaflex® (tizanidine) tablets with and without food. Secondarily, orthostatic hypotension as a side effect was assessed by measuring decreases from the supine to standing position of at least 20 mm Hg in systolic or 10 mm Hg in diastolic blood pressure.

The trials were conducted as a 4-way crossover study, with a single dose for each treatment period, and with a minimum 3-day washout period between study treatments. Up to 96 subjects were enrolled to ensure 80 subjects completed all 4 treatments. Healthy male or female volunteers, ages 18–55; within 20% of ideal body weight were enrolled in the study. The volunteers had normal values for systolic and diastolic blood pressures given their age and height. Eighty-eight subjects completed all 4 periods of the study. Pharmacokinetic parameters were calculated for all subjects who completed at least one treatment (N=96). Of the 96 subjects who participated in the study, 80 subjects were included in the summary statistics and statistical analysis of the pharmacokinetic parameters. Subjects who vomited during the 8 hours following the dose in one or more periods (N=3), subjects who did not complete all 4 periods (N=8), and subjects who were missing too many concentration data points within a period from one or more periods (N=5) were excluded from the statistical analysis of the pharmacokinetic parameters.

Test Product, Dose, Duration, and Mode of Administration, Batch Number

The test product was tizanidine (Treatment C and Treatment D) 2×4 mg capsules, manufactured by Elan Pharmaceutical Technologies, Lot No. PS1066P, expiration date, Nov. 10, 2001. Subjects randomized to Treatment C received a single oral dose of two tizanidine 4 mg capsules, with food, taken with 240 mL of water. Subjects randomized to Treatment D received a single oral dose of two tizanidine 4 mg capsules, fasted, taken with 240 mL of water.

Reference Product, Dose, Duration, and Mode of Administration, Batch Numbers: The reference product was Zanaflex® (tizanidine hydrochloride) (Treatment A and Treatment B) 2×4 mg tablets, manufactured by Brecon Pharmaceutical Limited, Lot No. 197MFD1299, expiration date, Dec. 31, 2004. Subjects randomized to Treatment A received a single oral dose of two Zanaflex® 4 mg tablets, with food, taken with 240 mL of water. Subjects randomized to Treatment B received a single oral dose of two Zanaflex® 4 mg tablets, fasted, taken with 240 mL of water.

Cognitive Assessment: Simple Reaction Time, Digit Vigilance Task, Choice Reaction Time, Bond-Lader Visual Assessment Scale of Mood and Alertness were assessed at pre-dose, 0.75, 1.5, 2.5, and 6 hours post-dose. See the statistical methods section below for a discussion of the cognitive assessment system and its application.

Pharmacokinetic Evaluation: Plasma concentrations of tizanidine were determined following the single dose administration of each treatment (Treatment A: 2×4 mg tizanidine tablets with food, Treatment B: 2×4 mg tizanidine tablets without food, Treatment C: 2×4 mg tizanidine capsules with food, and Treatment D: 2×4 mg tizanidine capsules without food). The pharmacokinetic parameters Cmax, Tmax, AUC (0-t), AUC(0-inf), were calculated using noncompartmental methods.

Safety parameters assessed included medical history, physical examination, vital signs, orthostatic hypotension, 12-lead ECGs, clinical laboratory testing, adverse events, and cognitive assessment.

Statistical Methods:

Cognitive Assessment: The Cognitive Drug Research assessment system as used in this study has been described in elsewhere, e.g. Wesnes, K. A.; Garratt, C.; Wickens, M.; Gudgeon, A.; Oliver, S.; Effects of sibutramine alone and with alcohol on cognitive function in healthy volunteers, British Journal of Pharmacology, 49: 110–117 (2000) and Simpson, P. M.; Surmon, D. J.; Wesnes, K. A.; and Wilcock, G. R., The congnitive drug research computerised assessment system for demented patients: A validaiton study. International Journal of Geriatric Psychiatry 6: 95–102 (1991). Power of Attention was determined by the summation of scores from Simple Reaction Time, Digit Vigilance Task, and Choice Reaction Time. Degree of somnolence was derived from Self-rated Alertness, Self-rated Contentedness, and Self-rated Calmness formed from the Bond-Lader VAS scores. ANOVA model was used to detect treatment differences. The tests employed in conducting the assessment measure major aspects of cognitive function. The attentional tests are highly sensitive to fluctuations in the levels of alertness, which influence the ability to conduct everyday tasks such as driving.

Pharmacokinetic Evaluation: Plasma concentrations and pharmacokinetic parameters were summarized by treatment using summary statistics. A parametric, normal-theory general linear model was applied to the untransformed and log-transformed Cmax, AUC(0-t), and AUC(0-inf) parameter values. The primary comparisons were Treatment C versus Treatment A, Treatment D versus Treatment B, and Treatment C versus Treatment D. Comparisons of Tmax were made using the Wilcoxon Signed Rank test.

Cognitive Assessment Results: The impairment in Power of Attention following capsules taken under fed conditions showed a delay of onset compared with the tables taken under fed conditions and capsules and tablets taken under fasted conditions. There was no impairment at 0.75 hours following capsules taken under fed conditions while the impairment was significant with the other three dosing groups. At 1.5 hours and 2.5 hours post dose, performance was impaired under all four dosing groups to a lesser extent than at 0.75 hours and the effect resolved completely by 6 hours post dose. The secondary measures showed the same pattern of change as Power of Attention.

Pharmacokinetic (PK) Results: Median and mean pharmacokinetic parameters following the four treatment regimens are shown in Table I

TABLE I

Pharmacokinetic Data
Tizanidine Tablet/Capsule Study

| PARAMETER | Treatment A | Treatment B | Treatment C | Treatment D |
|---|---|---|---|---|
| $T_{max}$ (hr) Median value | 1.41 | 1.00 | 3.00 | 1.01 |
| $C_{max}$ (ng/mL) Mean value | 6.80 [0.25] | 5.43 [0.25] | 4.57 [0.25] | 5.36 [0.25] |
| $AUC_{last}$ (ng * hr/mL) Mean value | 20.31 [0.99] | 15.78 [0.99] | 17.43 [0.99] | 15.99 [0.99] |
| $AUC_{inf}$ (ng * hr/mL) Mean value | 22.08 [1.82] | 19.54 [2.01] | 20.83 [2.54] | 18.01 [2.12] |

Treatment:
A = 2 × 4 mg Tizanidine Tablets with food
B = 2 × 4 mg Tizanidine Tablets without food
C = 2 × 4 mg Tizanidine Capsules with food
D = 2 × 4 mg Tizanidine Capsules without food
Values in brackets are the standard error Values in brackets are the standard error The values for Tmax were statistically compared between treatments and the median Tmax for the tablet fasted (1.0 hr) and capsule fasted (1.01 hr) were not different (p=0.0601). The median Tmax for the capsule fed (3.0 hr) was significantly later than that for the tablet fed (1.41 hr) (p<0.0001) where p is Student's T value.

Fasted administration of the capsule achieved a mean Cmax of 5.36 ng/mL at 1.01 hr compared to a mean Cmax of 5.43 ng/mL at 1.00 hr for the tablets administered in the fasted state. The AUC(0-t) of the capsule (15.99 ng*hr/mL) administered in the fasted state were similar. The tizanidine capsule met the established criteria for bioequivalence to the Zanaflex® tablet in the fasted state with respect to Cmax and AUC(0-t) in that there was no significant difference in either of the these parameters. The AUC(0-inf) values could not be calculated for a meaningful number of subjects in each treatment. The median Tmax values for the fasted capsule and tablet treatments were nearly identical (1.01 hr for the capsule and 1.0 hr for the tablet, p=0.077).

The pharmacokinetic study confirmed the bioequivalence, as defined by FDA guidelines, of the tizanidine capsule formulation and the Zanaflex® tablet in the fasted state. In the absence of a dose that would be within the range that would elicit the effects being studied, it is not appropriate to conclude that there is no absolute qualitative difference in effect between the tablet and capsules and the presence of food. It is clear, however, that the maximal plasma concentrations and extent of absorption in the presence of food are more marked for the tablet than the capsule.

The food effect on the PK parameters of tizanidine following the capsule administration was appreciable, as it resulted in an approximately 20% difference in Cmax and AUC(0-t) compared to administration in the fasted state. The results for the Zanaflex® tablet, however, showed a more marked effect with Cmax approximately 23% higher and AUC(0-t) approximately 45% higher when administered with food (analyzed using log transformed values).

Based on all safety data obtained during the study, administration of tizanidine tablets and capsules in fed and fasted conditions appeared to be safe and generally well tolerated by the healthy male and female subjects participating in the study. Asthenia and somnolence were the most common treatment-related side effects, following all treatments. Orthostatic hypotension was experienced during all treatment regimens by 24%–31% of subjects following dosing, with the majority of the episodes occurring between 1 and 2 hours post-dose. No treatment-related differences were noted for adverse events, clinical laboratory parameters, ECGs, or physical examinations.

The reformulation of tizanidine into a multiparticulate capsule resulted in a reduced food effect on Cmax and AUC compared to the commercial tablet formulation. The effect of food causing an increase in the Cmax and AUC of tizanidine was diminished by the new capsule formulation. The capsule formulation also resulted in a greater delay in absorption (median 2 hours) when administered with food compared to the tablet formulation (median 25 minutes). Administration of tizanidine tablets and capsules in fed and fasted conditions appeared to be safe and generally well tolerated by the healthy male and female subjects participating in the study.

The following non-limiting examples are provided by way of illustration, and are not to intended to construe the scope of the invention.

Multiparticulate Pharmaceutical Compositions

Description of Individual Process Steps

| Stage | Description | Summary |
|---|---|---|
| 1 | Application Solution | Manufacture of application solution containing active, anti adherent, binder and purified water. |
| 2 | Immediate Release Multiparticulates | Application of solution from Stage 1 onto inert sugar spheres (non-pareil beads) to form drug loaded multiparticulates. |
| 3 | Encapsulation/ Weight sorting | Encapsulation of the multiparticulates from Stage 2 to achieve a unit dose of the formulation. Weight sorting of encapsulated product. |

For the manufacture of the Tizanidine HCl Application Solution, the relevant excipients were firstly weighed out. The binder (i.e., hydroxypropyl methylcellulose 3 cps) was mixed with purified water for at least 30 minutes or until completely dissolved. The active was then added and mixed for a further 15 minutes to form a solution. The anti adherent (i.e., silicon dioxide) was added finally, and mixed for a further 15 minutes.

For the manufacture of the Tizanidine HCl IR Multiparticulates, the Application Solution and the non-pareils (0.85–1.00 mm) were weighed. The non-pareils were preconditioned in the Glatt GPCG 30 (Glatt, Protech Ltd., Leicester, UK) fluid bed coating apparatus by placing the beads in the Glatt chamber, fluidised using air, and heated until the bypass temperature reached 55° C. The required amount of application solution was applied using the standard Glatt Wurster Process to achieve a target potency of 26.6 mg tizanidine per gram of multiparticulates. The target product temperature was 37° C. (Range 32–42° C.). An atomising air pressure of 2.0 bar was used. The spray rate and inlet temperature were adjusted to achieve the required product temperature. The applied beads were dried for a further 10 minutes in the Glatt, allowed to cool for 5 minutes, and then discharged into HDPE containers. They were stored with desiccant.

For the manufacture of Tizanidine HCl IR Capsules, the required amount of IR Beads was filled into hard gelatin capsules. Size 3 capsules were used for the 2 mg and 4 mg strengths. Size 2 capsules were used for the 6 mg strength. The different capsule strengths were achieved by encapsulating the multiparticulates at different final fill weights. The filled capsules were then checkweighed.

EXAMPLE 1

(a) Immediate Release Multiparticulates

A Tizanidine HCl Application Solution was prepared as described in the Description of Individual Process Steps above according to the formulation in Table 1. The Tizanidine HCl Application Solution was then coated onto non-pareil seeds to a level of approximately 9.5% solids weight gain using a Glatt GPCG 30 (Glatt, Protech Ltd., Leicester, UK) fluid bed coating apparatus to form Immediate Release Multiparticulates as described in the Description of Individual Process Steps above.

TABLE 1

Tizanidine HCl Application Solution

| Ingredient | Amount (% w/w) |
|---|---|
| Tizanidine HCl (Novartis) | 3.59 |
| Hydroxypropyl Methylcellulose 3 cps (Shin Etsu Chemical Co Ltd) | 4.96 |
| Silicon Dioxide (USP grade, W. R. Grace & Co.) | 1.65 |
| Purified Water | 89.79 |

(b) Immediate Release Capsules

The Immediate Release Multiparticulates prepared according to Example 1(a) above were encapsulated into hard gelatin capsules (Capsugel Colmar, Colmar France) to the required dosage strength as described in the Description of Individual Process Steps above.

TABLE 2

| | Immediate Release Capsules | | | | | |
|---|---|---|---|---|---|---|
| | 2 mg Capsule | | 4 mg Capsule | | 6 mg Capsule | |
| Ingredient | mg/ capsule | % w/w | mg/ capsule | % w/w | mg/ capsule | % w/w |
| Tizanidine HCl | 2.29 mg | 3.0 | 4.58 mg | 3.0 | 6.87 mg | 3.0 |
| Hydroxypropyl Methylcellulose 3 cps | 3.16 mg | 4.2 | 6.32 mg | 4.2 | 9.48 mg | 4.2 |
| Silicon Dioxide | 1.05 mg | 1.4 | 2.10 mg | 1.4 | 3.15 mg | 1.4 |
| Non Pareil Beads | 68.7 mg | 91.4 | 137.4 mg | 91.4 | 206.1 mg | 91.4 |

For dissolution testing, USP type II (rotating paddles) dissolution apparatus was employed at 50 rpm using 500 ml 0.01M HCl maintained at 37±0.5° C. The final capsule had not less than 75% released after 0.5 hrs.

EXAMPLE 2

(a) Immediate Release Multiparticulates

A Tizanidine HCl Application Solution is prepared as described in the Description of Individual Process Steps above according to the formulation in Table 3. The Tizanidine HCl Application Solution is then coated onto non-pareil sseds to a level of approximately 7.0% solids weight gain using for example a Glatt GPCG 5 (Glatt, Protech Ltd., Leicester, UK) fluid bed coating apparatus to form Immediate Release Multiparticulates as described in the Description of Individual Process Steps above.

TABLE 3

Tizanidine HCl Application Solution

| Ingredient | Amount (% w/w) |
|---|---|
| Tizanidine HCl | 3.59 |
| Hydroxypropyl Methylcellulose 6 cps | 2.50 |
| Silicon Dioxide | 1.65 |
| Purified Water | 92.26 |

Immediate Release Capsules

The Immediate Release Multiparticulates prepared according to Example 2(a) above are encapsulated into hard gelatin capsules to the required dosage strength as described in the Description of Individual Process Steps above.

TABLE 4

Immediate Release Capsules

| | 2 mg Capsule | | 4 mg Capsule | | 8 mg Capsule | |
|---|---|---|---|---|---|---|
| Ingredient | mg/capsule | % w/w | mg/capsule | % w/w | mg/capsule | % w/w |
| Tizanidine HCl | 2.3 mg | 3.0 | 4.6 mg | 3.0 | 9.2 | 3.0 |
| Hydroxypropyl Methylcellulose 6 cps | 1.6 mg | 2.1 | 3.2 mg | 2.1 | 6.4 | 2.1 |
| Silicon Dioxide | 1.1 mg | 1.4 | 2.2 mg | 1.4 | 4.4 | 1.4 |
| Non Pareil Beads | 71.4 mg | 93.5 | 152.7 mg | 93.5 | 305.4 | 93.5 |

For dissolution testing, USP type II (rotating paddles) is employed at 50 RPM using 500 ml 0.01M HCl maintained at 37±0.5° C. The final capsule has not less than 75% released after 0.5 hrs.

EXAMPLE 3

(a) Immediate Release Multiparticulates

A Tizanidine HCl Application Solution is prepared as described in the Description of Individual Process Steps above according to the formulation in Table 5. The Tizanidine HCl Application Solution is then coated onto non-pareil seeds to a level of approximately 9.5% solids weight gain using for example a Glatt GPCG 3 (Glatt, Protech Ltd., Leicester, UK) fluid bed coating apparatus to form Immediate Release Multiparticulates as described in the Description of Individual Process Steps above.

TABLE 5

Tizanidine HCl Application Solution

| Ingredient | Amount (% w/w) |
|---|---|
| Tizanidine HCl | 3.59 |
| Polyvinylpyrrolidone | 4.96 |
| Silicon Dioxide | 1.65 |
| Purified Water | 89.79 |

(b) Immediate Release Capsules

The Immediate Release Multiparticulates prepared according to Example 3(a) above are encapsulated into hard gelatin capsules to the required dosage strength as described in the Description of Individual Process Steps above.

TABLE 6

Immediate Release Capsules

| | 2 mg Capsule | | 4 mg Capsule | | 6 mg Capsule | |
|---|---|---|---|---|---|---|
| Ingredient | mg/capsule | % w/w | mg/capsule | % w/w | mg/capsule | % w/w |
| Tizanidine HCl | 2.29 mg | 3.0 | 4.58 mg | 3.0 | 6.87 mg | 3.0 |
| Polyvinylpyrrolidone | 3.16 mg | 4.2 | 6.32 mg | 4.2 | 9.48 mg | 4.2 |
| Silicon Dioxide | 1.05 mg | 1.4 | 2.10 mg | 1.4 | 3.15 mg | 1.4 |
| Non Pareil Beads | 68.7 mg | 91.4 | 137.4 mg | 91.4 | 206.1 mg | 91.4 |

For dissolution testing, USP type II (rotating paddles) is employed at 50 RPM using 500 ml 0.01M HCl maintained at 37±0.5° C. The final capsule has not less than 75% released after 0.5 hrs.

EXAMPLE 4

(a) Immediate Release Multiparticulates

A Tizanidine HCl Application Solution is prepared as described in the Description of Individual Process Steps above according to the formulation in Table 7. The Tizanidine HCl Application Solution is then coated onto nonpareil seeds to a level of approximately 8.6% solids weight gain using for example a Glatt GPCG 30 (Glatt, Protech Ltd., Leicester, UK) fluid bed coating apparatus to form Immediate Release Multiparticulates as described in the Description of Individual Process Steps above.

TABLE 7

Tizanidine HCl Application Solution

| Ingredient | Amount (% w/w) |
|---|---|
| Tizanidine HCl | 2.54 |
| Hydroxypropyl Methylcellulose 3 cps | 3.95 |
| Talc | 1.50 |
| Purified Water | 91.56 |

(b) Immediate Release Capsules

The Immediate Release Multiparticulates prepared according to Example 4(a) above are encapsulated into hard gelatin capsules to the required dosage strength as described in the Description of Individual Process Steps above.

TABLE 8

Immediate Release Capsules

| | 4 mg Capsule | | 6 mg Capsule | | 12 mg Capsule | |
|---|---|---|---|---|---|---|
| Ingredient | mg/capsule | % w/w | mg/capsule | % w/w | mg/capsule | % w/w |
| Tizanidine HCl | 4.56 | 2.5 | 6.84 | 2.5 | 13.68 | 2.5 |
| Hydroxypropyl Methylcellulose 3 cps | 7.09 | 3.9 | 10.64 | 3.9 | 21.28 | 3.9 |
| Talc | 2.73 | 1.5 | 4.10 | 1.5 | 8.2 | 1.5 |
| Non Pareil Beads | 167.44 | 92.1 | 251.16 | 92.1 | 502.32 | 92.1 |

For dissolution testing, USP type II (rotating paddles) is employed at 50 RPM using 500 ml 0.01M HCl maintained at 37±0.5° C. The final capsule has not less than 75% released after 0.5 hrs.

EXAMPLE 5

(a) Immediate Release Multiparticulates

A Tizanidine HCl Application Solution is prepared as described in the Description of Individual Process Steps above according to the formulation in Table 9. The Tizanidine HCl Application Solution is then coated onto non-pareil seeds to a level of approximately 8% solids weight gain using for example a Glatt GPCG 30 (Glatt, Protech Ltd., Leicester, UK) fluid bed coating apparatus to form Immediate Release Multiparticulates as described in the Description of Individual Process Steps above.

TABLE 9

| Tizanidine HCl Application Solution | |
| --- | --- |
| Ingredient | Amount (% w/w) |
| Tizanidine HCl | 7.00 |
| Hydroxypropyl Methylcellulose 3 cps | 4.00 |
| Talc | 2.50 |
| Purified Water | 79.50 |

(b) Immediate Release Capsules

The Immediate Release Multiparticulates prepared according to Example 5(a) above are encapsulated into hard gelatin capsules to the required dosage strength as described in the Description of Individual Process Steps above.

TABLE 10

| | Immediate Release Capsules | | | | | |
| --- | --- | --- | --- | --- | --- | --- |
| | 2 mg Capsule | | 4 mg Capsule | | 6 mg Capsule | |
| Ingredient | mg/capsule | % w/w | mg/capsule | % w/w | mg/capsule | % w/w |
| Tizanidine HCl | 2.5 | 2.5 | 5.0 | 2.5 | 7.5 | 2.5 |
| Hydroxypropyl Methylcellulose 3 cps | 1.4 | 1.4 | 2.8 | 1.4 | 4.2 | 1.4 |
| Talc | 1.2 | 1.2 | 2.4 | 1.2 | 3.6 | 1.2 |
| Fumaric acid | 2.5 | 2.5 | 5.0 | 2.5 | 7.5 | 2.5 |
| Non Pareil Beads | 90.6 | 92.4 | 181.2 | 92.4 | 271.8 | 92.4 |

For dissolution testing, USP type II (rotating paddles) is employed at 50 RPM using 500 ml 0.01M HCl maintained at 37±0.5° C. The final capsule has not less than 75% released after 0.5 hrs.

Article of Manufacture

The article of manufacture comprises a container holding an immediate release pharmaceutical composition suitable for oral administration of tizanidine in combination with printed labeling instructions providing a discussion of when a particular dosage form should be administered with food and when it should be taken on an empty stomach. The composition will be contained in any suitable container capable of holding and dispensing the dosage form and which will not significantly interact with the composition and will further be in physical relation with the appropriate labeling advising that an immediate release tablet dosage form has less somnolence associated with its use if taken on an empty stomach and an immediate release multiparticulate dosage form has less somnolence associated with its use if taken with food. The labeling instructions will be consistent with the methods of treatment as described hereinbefore. The labeling may be associated with the container by any means that maintain a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

While the invention has been described by discussion of embodiments of the invention and non-limiting examples thereof, one of ordinary skill in the art may, upon reading the specification and claims, envision other embodiments and variations which are also within the intended scope of the invention and therefore the scope of the invention shall only be construed and defined by the scope of the appended claims.

We claim:

1. A method of reducing somnolence in a patient receiving tizanidine therapy comprising administering to the patient a therapeutically effective amount of tizanidine in an immediate release multiparticulate pharmaceutical composition with food, wherein administration of the composition with food produces a peak plasma tizanidine concentration earlier than about 4 hours from administration.

2. The method of claim 1 wherein the therapeutically effective amount is 0.5 mg to 12 mg.

3. The method of claim 1 wherein the therapeutically effective amount is 2 mg to 8 mg.

4. The method of claim 1 wherein the administration to the patient occurs between 30 minutes prior to 2 hours after consuming food.

5. The method of claim 1 wherein the administration to the patient is substantially at the same time as the consumption of the food.

6. The method of claim 1 wherein the administration to the patient is immediately after the consumption of food up to 1 hour after said consumption.

7. The method of claim 1 wherein the immediate release multiparticulate formulation comprises a multiparticulate form of tizanidine on beads.

8. The method of claim 7 wherein the immediate release multiparticulate formulation is in unit dosage form.

9. The method of claim 8 wherein the unit dosage form contains from 2 to 6 milligrams of tizanidine.

10. A method of reducing the peak plasma concentration from an oral dosage form of tizanidine in a patient in need of a therapeutic effect thereof comprising administering to the patient a therapeutically effective amount of tizanidine in an immediate release multiparticulate pharmaceutical composition with food, wherein administration of the composition with food produces a peak plasma tizanidine concentration earlier than about 4 hours from administration.

11. The method of claim 10 wherein the therapeutically effective amount is about 0.5 mg to about 12 mg.

12. The method of claim 10 wherein the therapeutically effective amount is from about 2 mg to about 8 mg.

13. The method of claim 10 wherein the administration to the patient occurs between about 30 minutes prior to about 2 hours after consuming food.

14. The method of claim 10 wherein the administration to the patient is substantially at the same time as the consumption of the food.

15. The method of claim 10 wherein the administration to the patient is immediately after the consumption of food up to about one hour after said consumption.

16. The method of claim 10 wherein the immediate release multiparticulate formulation comprises a multiparticulate form of tizanidine on beads.

17. The method of claim 16 wherein the immediate release multiparticulate formulation is in unit dosage form.

18. The method of claim 17 wherein the unit dosage form contains from 2 to 6 milligrams of tizanidine.

19. A method of reducing the peak plasma concentration from an oral dosage form of tizanidine in a patient in need of a therapeutic effect thereof comprising administering to the patient a therapeutically effective amount of tizanidine in an immediate release multiparticulate pharmaceutical composition with food, wherein the composition produces a peak plasma tizanidine concentration earlier than about 2 hours from administration when administered without food.

20. A method of reducing the peak plasma concentration from an oral dosage form of tizanidine in a patient in need of a therapeutic effect thereof comprising administering to the patient a therapeutically effective amount of tizanidine in an immediate release multiparticulate pharmaceutical composition with food, wherein the composition releases substantially all of its tizanidine contents within 60 minutes of administration.

21. A method of reducing the peak plasma concentration from an oral dosage form of tizanidine in a patient in need of a therapeutic effect thereof comprising administering to the patient a therapeutically effective amount of tizanidine in an immediate release multiparticulate pharmaceutical composition with food, wherein the composition releases at least 75% of its tizanidine contents within 60 minutes of administration.

* * * * *

UNITED STATES PATENT AND TRADEMARK OFFICE
CERTIFICATE OF CORRECTION

PATENT NO. : 6,455,557 B1
DATED : September 24, 2002
INVENTOR(S) : Cara A. Pellegrini et al.

It is certified that error appears in the above-identified patent and that said Letters Patent is hereby corrected as shown below:

Title page,
Item [56], OTHER PUBLICATIONS, "45(12);2296-2296" should read -- 45(12): 2296-2296 --.
"*Hospice&*" should read -- *Hospice &* --.

Column 1,
Line 5, "is invention" should read -- This invention --.

Column 2,
Line 21, "Smith H S; Barton A E," should read -- Smith HS; Barton AE, --.

Column 5,
Line 32, "gylcerol" should read -- glycerol --.

Column 7,
Line 28, "validaiton" should read -- validation --.

Column 8,
Line 37, "of the these parameters" should read -- of these parameters --.

Column 9,
Line 19, "not to intended" should read -- not intended --.

Column 12,
Line 24, "nonpareil" should read -- non-pareil --.

UNITED STATES PATENT AND TRADEMARK OFFICE
CERTIFICATE OF CORRECTION

PATENT NO.   : 6,455,557 B1
DATED        : September 24, 2002
INVENTOR(S)  : Cara A. Pellegrini et al.

It is certified that error appears in the above-identified patent and that said Letters Patent is hereby corrected as shown below:

Column 13, Table 9, line 15, above
 "Talc                 2.50" insert
 -- Fumaric acid       7.00 --.

Signed and Sealed this

Twenty-ninth Day of April, 2003

JAMES E. ROGAN
*Director of the United States Patent and Trademark Office*